(12) United States Patent  (10) Patent No.: US 7,569,075 B2
Johnson et al.  (45) Date of Patent: Aug. 4, 2009

(54) THRUST PLATE HIP PROSTHESIS (76) Inventors: James F. Johnson, 2301 25th St. South, Ste., Fargo, ND (US) 58103; James J - S Stone, 3805 Westmoor Dr., Moorhead, MN (US) 56560

( * ) Notice: Subject to any disclaimer, the term of this patent is extended or adjusted under 35 U.S.C. 154(b) by 469 days.

(21) Appl. No.: 11/212,864

(22) Filed: Aug. 26, 2005

(65) Prior Publication Data

US 2007/0255420 A1  Nov. 1, 2007

(51) Int. Cl.
  *A61F 2/32* (2006.01)
(52) U.S. Cl. .............. 623/22.41; 623/22.42; 623/22.44; 623/22.46
(58) Field of Classification Search .............. 623/23.14, 623/20.35, 20.36, 22.44, 23.21, 23.26, 23.29; 606/65–67
  See application file for complete search history.

(56) References Cited

U.S. PATENT DOCUMENTS

| 2,718,228 | A | * | 9/1955 | Van Steenbrugghe .... 623/23.14 |
| 3,765,034 | A | | 10/1973 | Johnston |
| 4,005,495 | A | | 2/1977 | Locke et al. |
| 4,101,985 | A | * | 7/1978 | Baumann et al. ......... 623/22.46 |
| 4,795,473 | A | | 1/1989 | Grimes |
| 4,998,937 | A | | 3/1991 | Grimes |
| 5,007,935 | A | | 4/1991 | Vincent et al. |
| 5,362,311 | A | * | 11/1994 | Amino et al. ............ 623/22.45 |
| 5,376,125 | A | | 12/1994 | Winkler |
| 5,571,203 | A | | 11/1996 | Masini |
| 5,658,339 | A | | 8/1997 | Tronzo et al. |
| 5,725,597 | A | * | 3/1998 | Hwang ..................... 623/22.15 |
| 5,800,553 | A | * | 9/1998 | Albrektsson et al. ....... 623/22.4 |
| 5,810,821 | A | | 9/1998 | Vandewalle |
| 6,695,883 | B2 | * | 2/2004 | Crofford .................. 623/22.46 |
| 6,706,073 | B2 | | 3/2004 | Draenert et al. |
| 2001/0049561 | A1 | * | 12/2001 | Dews et al. .............. 623/19.14 |
| 2003/0171819 | A1 | * | 9/2003 | Sotereanos ............... 623/22.42 |

OTHER PUBLICATIONS

H.A.C. Jacob, Biomechanical Principles and Design Details of the Thrust Plate Prosthesis, p. 37.

* cited by examiner

*Primary Examiner*—Thomas J Sweet
*Assistant Examiner*—Yashita Sharma
(74) *Attorney, Agent, or Firm*—D L Tschida (57) ABSTRACT

A hip joint prosthesis that has a strap plate and a hollow, tapered femoral neck subassembly. The femoral neck includes a flanged force plate that radiates from a head stem base and abuts the femur. Several longitudinal ridges and/or an annular recess or other surface treatment at the head stem base facilitates retention in the femur. Shaped surfaces of a femoral neck at the strap plate interlock in non-rotational engagement with a bore of the head stem base. A tapered stem projects from the force plate and supports a ball head. The strap plate includes laterally and longitudinally displaced elongated fastener holes and stress relieving recesses and/or channels. Fasteners anchor the strap plate to the femoral shaft. A shouldered bolt mounts through the femoral neck to engage the ball head base and draw the ball head base and ball head toward the strap plate and contain the prosthesis to the femur.

14 Claims, 13 Drawing Sheets

FIG. 16

THRUST PLATE HIP PROSTHESIS

BACKGROUND OF THE INVENTION

The present invention relates to a hip prosthesis and, in particular, to a ball-type prosthesis having a head stem base that mounts in a femoral recess and supports a ball head, which stem base is secured to the femur with a strap and a femoral neck that interlocks with the head stem base.

A variety of prostheses have been developed to repair and alleviate degenerating hip joints. Efforts have been extended to developing artificial sockets for attachment to the hip and interlocking artificial ball heads for the femur. The day-to-day stresses placed on the prosthesis and joint members present a variety of collective concerns and considerations that must be addressed to facilitate prosthetic installation and achieve long lasting integrity.

Several ball joint, hip replacement systems are disclosed in the patent literature. U.S. Pat. No. 3,765,034 discloses a prosthesis having a tapered spindle that mounts in the femur. An external drill guide plate separately aligns a series of screws to the spindle. U.S. Pat. No. 4,101,985 patent discloses a washer plate and through which a bolt is fitted and mounts to a ball head.

Several systems shown at U.S. Pat. Nos. 5,007,935; 5,376,125; 5,658,339; and 5,810,821 provide plates that fasten with screws to the shank of the femur. Bored sleeve or barrel pieces project from the fastener plates and support concentric fasteners that fasten to a ball head and draw the head to the femur.

U.S. Pat. No. 5,800,553 patent provides a screw fastened external plate with a series of end couplers that collectively extend to a ball head. The couplers include internal and external threads.

The present invention was developed to provide an improved hip prosthesis that optimally distributes the stress and loading to extend implant life. The assembly includes a thrust or strap plate that mounts to the femur with a number of screws mounted to elongated, laterally displaced holes. Stress relieving features are included at the plate. A bored, femoral neck or stein piece transversely extends from the plate (e.g. at an obtuse or oblique angle) and interlocks in non-rotational engagement with a tapered, ball head stem base. A shouldered bolt draws the femoral neck to interlock with the bore of the ball head base as a flanged force plate is drawn into abutment with the femur, whereby the ball head base is secured in a surgically prepared femoral recess. The pieces are constructed from or coated with a material that exhibits a suitable surface porosity, sintering or other abrading material, for example a cobalt-chromium alloy (CrCo) having a yield strength in the range of 35 ksi to 230 ksi, stainless steel, titanium or other biocompatible material.

SUMMARY OF THE INVENTION

It is a primary object of the present invention to provide a hip joint prosthesis and in particular a ball joint for reconstruction of the femoral acetabular joint.

It is a further object of the present invention to provide a prosthesis that screw fastens to the femur at a thrust or strap plate and that is coupled to a tapered, head stem base that is embedded in the end of the femur.

It is a further object of the invention to provide a strap plate with at least one stress relieving feature (e.g. a recess) to distribute stress away from the femoral neck.

It is a further object of the invention to provide a strap plate with a number of offset, elongated fastener holes.

It is a further object of the invention to provide a strap plate with a number of offset, stress relieving surface treatments (e.g. recesses).

It is a further object of the invention to provide a hollow, tapered, femoral neck stem base with a bore that interlocks in non-rotating engagement with a femoral neck or stem piece of the strap plate.

It is a further object of the invention to provide a hollow, tapered, femoral neck stem base with a head stem neck that mates with interchangeable ball heads having mounting bores of different depths and/or tapers.

It is a further object of the invention to provide a hollow, tapered femoral neck stem base with a flanged force plate and several alternatively configured longitudinal interruptions (e.g. tapered ridges) and/or annular recess(es).

It is a further object of the invention to provide a shouldered fastener that mounts through the femoral neck of the strap plate and interlocks with and draws the head stem base into engagement with the femur.

The foregoing objects, advantages and distinctions of the invention, among others, are found in a presently preferred assembly that provides a hip joint prosthesis that has a bored, tapered femoral neck stem base that embeds within the femur and a flanged force plate that abuts the femur. Several external longitudinal interruptions (e.g. tapered ridges and an annular recess) are formed into the head stem base to promote adhesion to the femur, in-growth and dispersion of adhesives. A tapered, femoral neck stem piece projects from the force plate and supports an interchangeable ball head.

A stem plate has a bored, femoral neck or stem piece that projects in an approximate range of 120° to 135° from a strap plate and mounts in the head stem base. Laterally and longitudinally displaced elongated fastener holes and stress relieving recesses and/or channels are provided at the strap plate. The femoral neck and head stem base include several shaped surfaces that interlock in non-rotational engagement.

The strap plate is anchored to the femoral shaft with several fasteners fitted through offset apertures. A shouldered bolt mounts through the femoral neck or stem piece and provides threads that engage the head stem base to draw the head stem base and ball head together and such that the flange plate engages the femur. The ball head mounts to a head stem that projects from the flange plate and has a desired Morris taper that is compatible with a taper and bore at an interchangeable ball head.

Still other objects, advantages and distinctions of the invention will become more apparent from the following description with respect to the appended drawings. Considered alternative constructions, improvements or modifications are described as appropriate. The singular features may also be combined into a variety of different combinations. The following description should therefore not be literally construed in limitation of the invention. Rather, the scope of the invention should be broadly interpreted within the scope of the further appended claims.

DESCRIPTION OF THE PREFERRED EMBODIMENT

Figure 1:
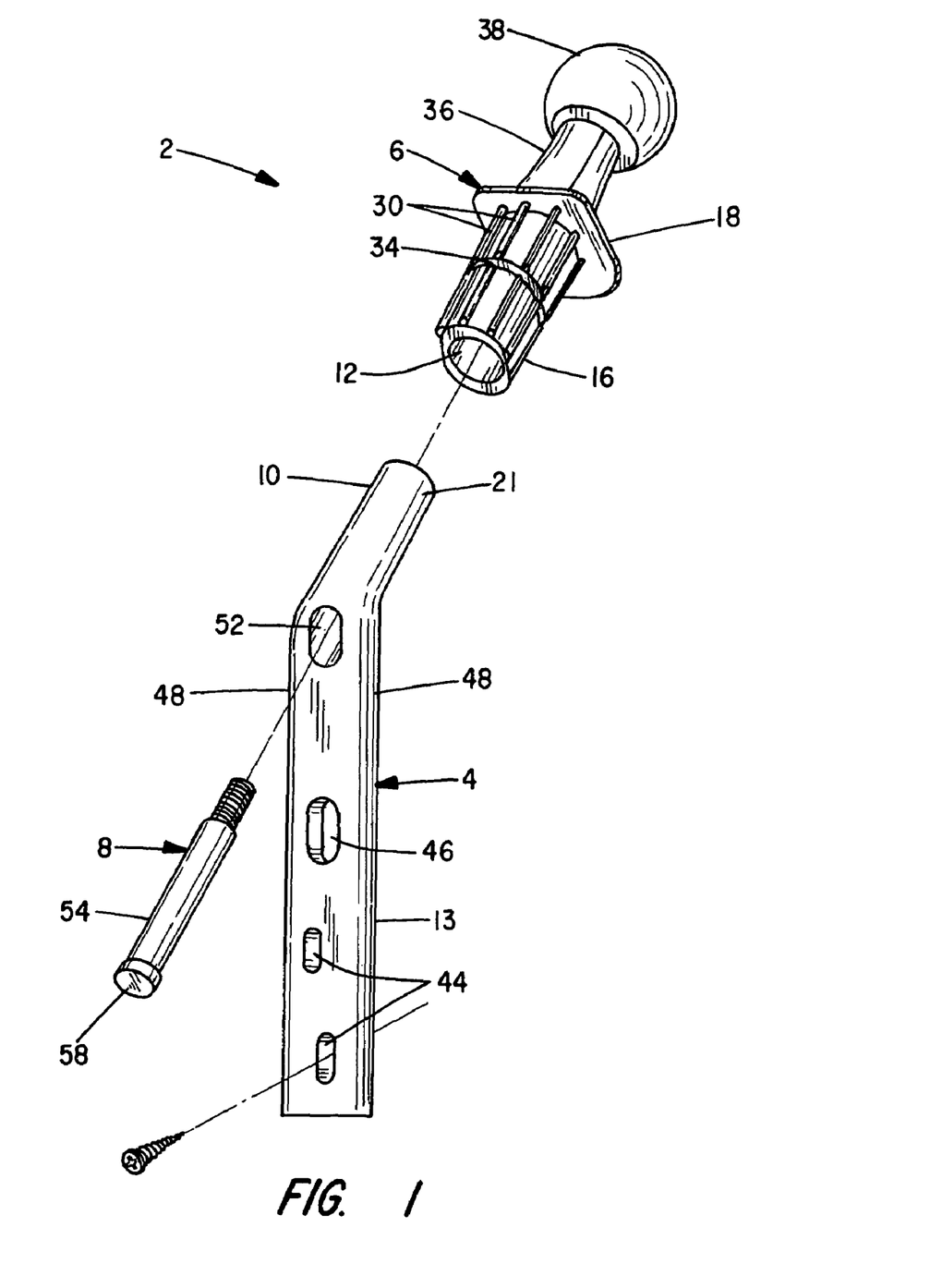
FIG. 1 shows a perspective view in exploded assembly of the prosthesis of the invention.

With attention to FIG. 1, a perspective view is shown in exploded assembly to the hip joint prosthesis assembly 2 of the invention. The assembly 2 includes a strap or thrust plate 4, a ball head or femoral neck subassembly 6 and a draw fastener 8. In normal use and by way of a general overview to the method of installation of the assembly 2, a recess (not shown) is surgically formed in the end of the femoral shaft. The femoral shaft recess is prepared to receive the ball head subassembly 6.

Figure 2:
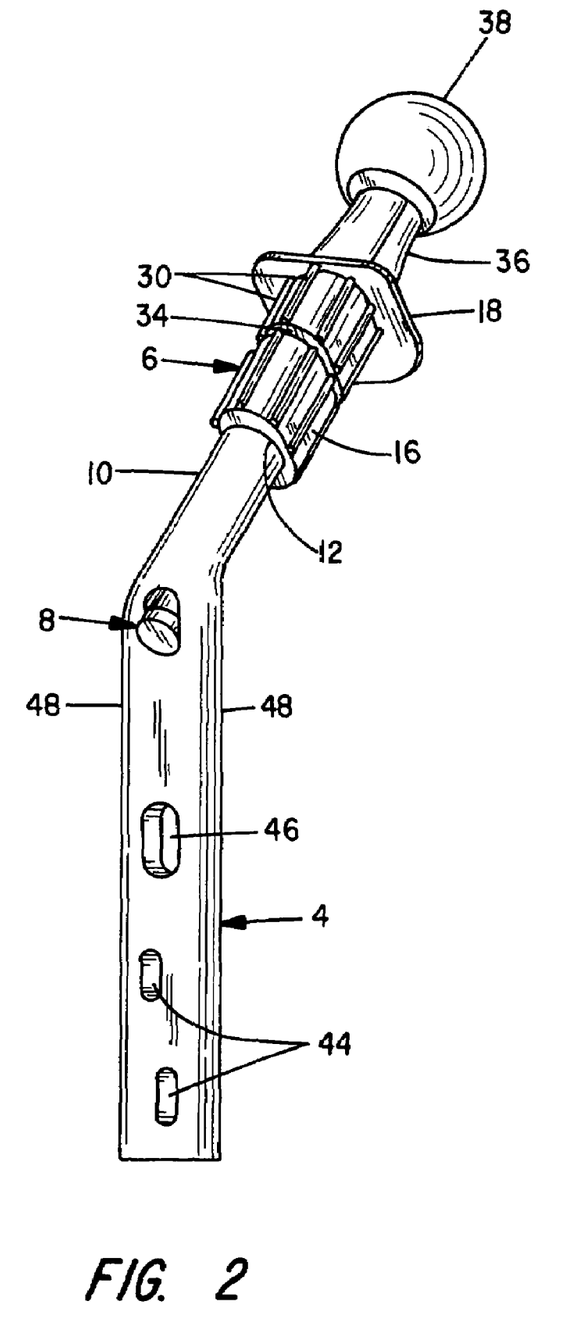
FIG. 2 shows a perspective, assembled view of the prosthesis of the invention.

An aperture (not shown) is also formed in the sidewall of the femoral shaft that communicates with the recess. A femoral neck or stem piece 10 of the strap plate 4 is fitted through the femur bore to mount in a hollow cavity 12 of the ball head subassembly 6. A strap piece 13 of the strap plate 4 is secured to the shank of the femur with several appropriate bone screw fasteners 14. The femoral neck 10 projects in an approximate range of 120° to 135° from the strap piece 13. The draw fastener 8 is fitted into the stem piece 10 and rotated to engage mating threads in the ball head subassembly 6 and draw the ball head subassembly 6 into the femoral shaft recess. The assembled prosthesis 2 is shown in FIG. 2.

The thrust plate 4, ball head subassembly 6 and draw fastener 8 can be constructed from or coated with a variety of materials. The presently preferred assembly 2 is constructed from a cobalt-chromium alloy (CrCo) having a yield strength in the range of 35 ksi to 230 ksi. The pieces 4, 6 and/or 8 can alternatively be constructed of various other materials (e.g. stainless steel, titanium or other biocompatible materials) and/or coated with still other biocompatible materials to promote bone in-growth and/or enhance the fixation of an associated adhesive and/or fixative and/or provide reduced wear at the assembly 2 and femoral acetabulum. Preferably and among several considerations, the materials should be compatible with normal sterilization processes, promote tissue and bone in-growth and sustain the anticipated loading and working force requirements without undue flexion or movement at the various orientations encountered during normal walking, exercise etc. of an active user.

Figure 3:
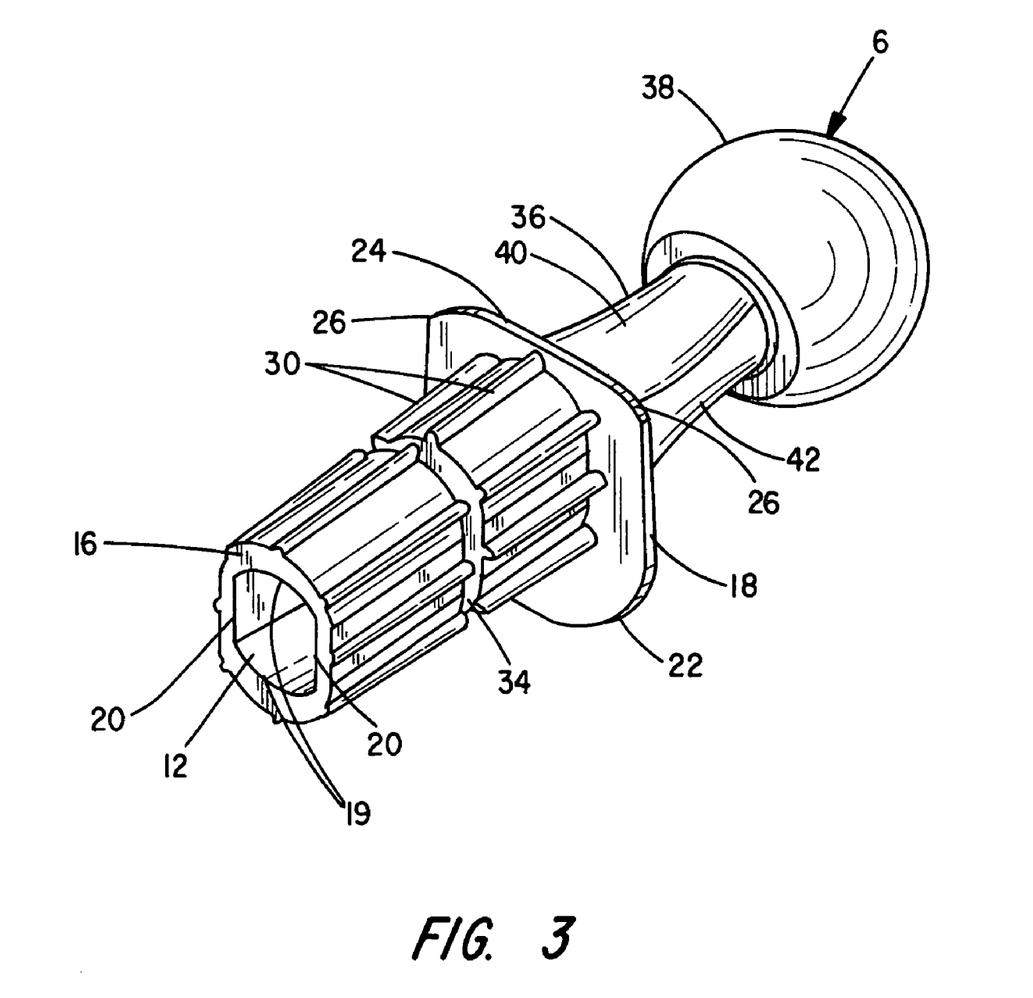
FIG. 3 shows a perspective view of the ball head assembly.
Figure 4:
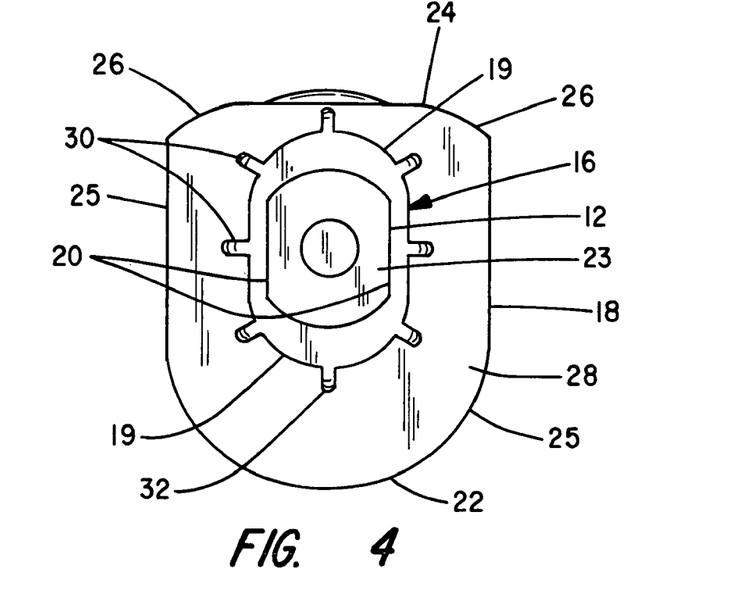
FIG. 4 shows a plan view of the alignment of the stem piece at the ball head base relative to the force plate.
Figure 5:
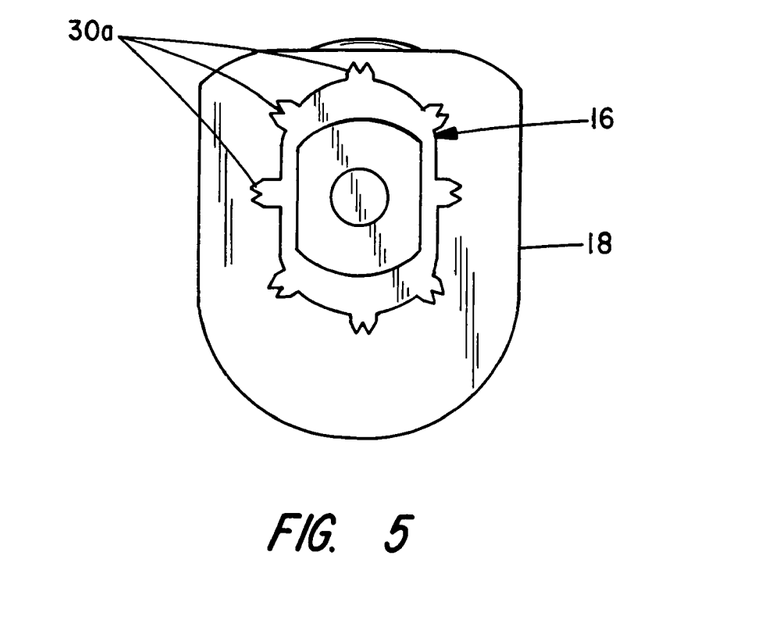
FIG. 5 shows a plan view to a stem piece at the ball head having a first alternative ridge configuration.
Figure 6:
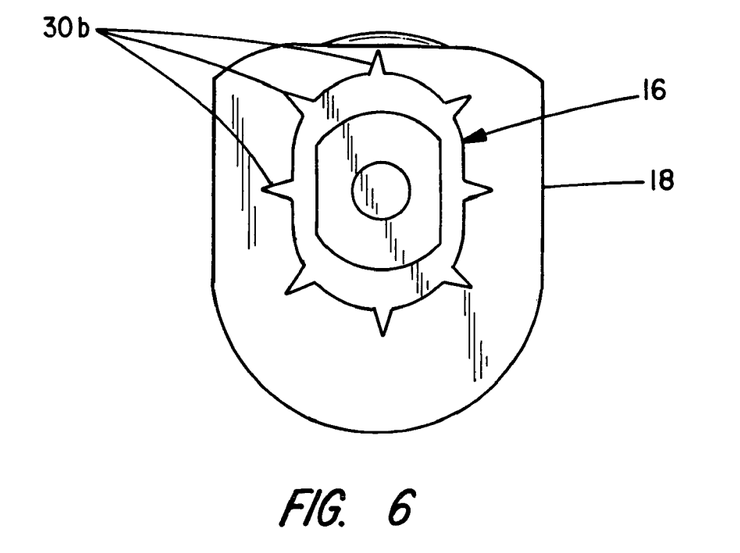
FIG. 6 shows a plan view to a stem piece at the ball head having a second alternative ridge configuration.
Figure 7:
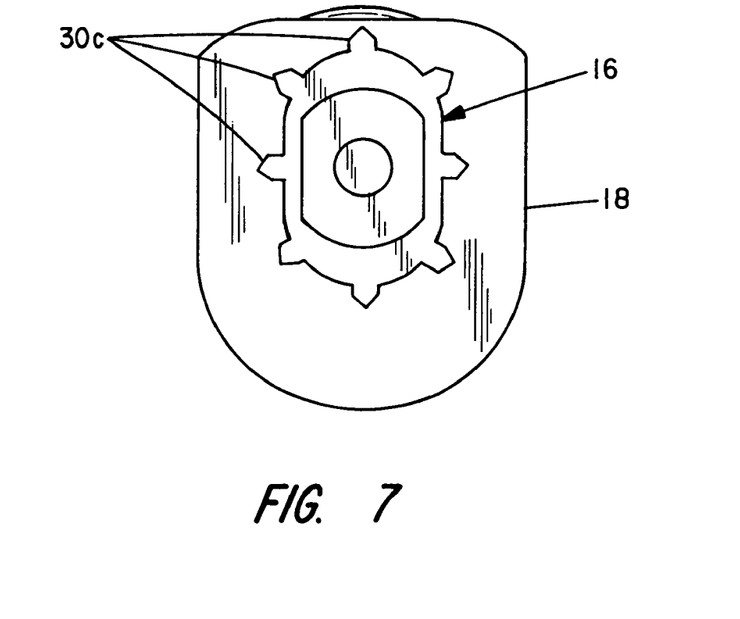
FIG. 7 shows a plan view to a stem piece at the ball head having a third alternative ridge configuration.
Figure 8:
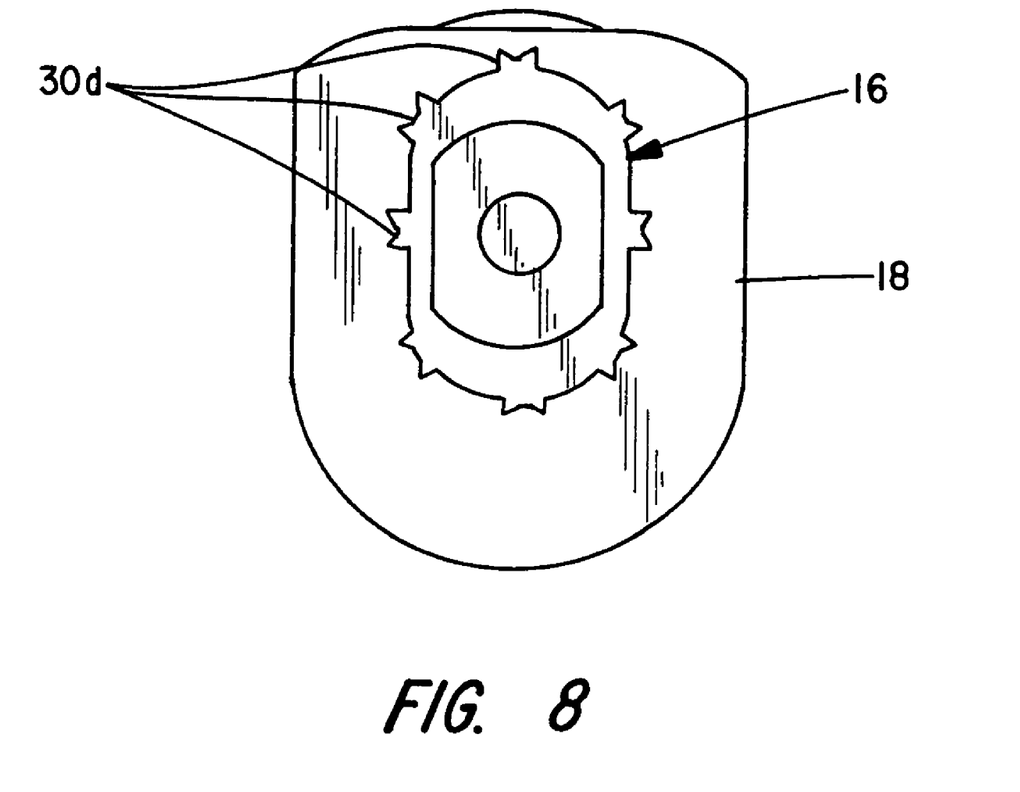
FIG. 8 shows a plan view to a stem piece at the ball head having a fourth alternative ridge configuration.

With attention to the individual pieces of the prosthesis assembly 2, FIGS. 3 and 4 depict details to the femoral neck subassembly 6. The femoral neck subassembly 6 is formed to include a tapered, head stem base 16 having a longitudinal stem bore 12. The outer surface of the head stem base 16 exhibits a taper that increases in a range of 0 to 15° as it extends from a distal end to a proximal end at the thrust or force plate 18. The width and length are varied to accommodate various nominal ranges of different femur sizes. The force plate 18 abuts the surgically prepared end of a femur. The head stem base 16 and force plate 18 define a calcar component of the femoral neck subassembly 6.

The bore 12 is formed with several flat, sidewall surfaces 20, interconnected by arcuate surfaces 19. The surfaces 19 and 20 cooperate with mating flat surfaces 21 at the femoral neck or stem piece 10 to prevent relative rotation of the stem piece 10 within the bore 12. A variety of different compound circumferential profiles or geometric arrangements and/or tapers can be formed at the stem bore 12, stem piece 10 and surfaces 20 and 21 to facilitate a draw action and prevent relative rotation. The interior of the stem bore 12 is also shaped to include an end stop surface 23 (e.g. an annular flanged ridge). The surface 23 is compatible with the distal end of the stem piece 10 to accommodate an anticipated maximum mounting depth.

The force plate 18 limits the mounting depth of the femoral neck 10 in the head stem base 16. The plate 18 exhibits an elongated, generally rectangular shape. The one edge 22 exhibits a full radius and the opposite edge 24 provides cornered radiuses 26 that intersect with flat side edges 25, reference FIG. 4. The stem base 16 is offset along a longitudinal center axis "A" toward the edge 24 from a longitudinal axis "B" through the center of the plate 18. The distance of the offset can be varied. The plate 18 is thus offset relative to the longitudinal center axis "B" of the stem base and the mating recess surgically formed in the femur.

The inner surface 28 that abuts the prepared end of the femur is also shaped and sized to distribute the compressive fastening forces away from the femoral mounting recess to prevent splintering, cracking etc. at the femur. The surface 28 is presently flat, although can exhibit an appropriate compound and/or convex shape that closely complements the adjoining mounting surface at the femur.

With attention to FIG. 4, a number of longitudinally arranged interruptions, for example, ridges 30, radially project around the head stem base 16. Each ridge 30 protrudes from an outer surface of the stem base 16. Each ridge 30 tapers in a range over its length on the order of 0.02-inch to 0.1-inch and exhibits a peripheral edge 32. The ridges 30 may also be formed to a uniform height over their length. The number, spacing between and placement of the ridges 30 can be varied as desired to facilitate mounting and retention of the head stem base 16 to the prepared femoral shaft.

Each edge 32 is shaped to facilitate insertion and attachment to the femoral recess. The configuration of the edge 32 can be varied to facilitate bone penetration (e.g. an inverted u-shape, v-shape or w-shape) when the stem base 16 is set and/or drawn into the surgically prepared femoral recess. Channels (not shown) that extend longitudinally or transversely might also be let into the outer surface of the head stem base 16 in lieu of and/or in addition to the ridges 30. FIGS. 5, 6, 7 and 8 depict alternatively shaped ridges 30a, 30b, 30c and 30d.

In the latter regard, let into the head stem base 16 is an annular groove 34 collectively defined by interruptions in the ridges 30 that transect each ridge 30 (e.g. at 90°) approximately mid-length along the ridges 30. Multiple grooves 34 can be provided as desired. The grooves 34 may also be recessed into the outer surface of the head stem base 16. Perforations or dimpled recesses might also be provided intermediate the ridges 30. The ridges 30, grooves 34 and other surface detailing are provided to facilitate bone ingrowth and/or accept an appropriate bonding fixative to further enhance fixation of the assembly 2.

Projecting from the forward or distal surface of the force plate 18 is a tapered head stem 36. A ball head 38 is formed or mounted to the distal end of the head stem 36. A detachable ball head 38 is presently mounted to the head stem 36. The head stem 36 and ball head 38 define a femoral neck component of the ball head subassembly 6. The ball head 38 is constructed as a generally spherical piece and exhibits a radius in the range of 22 mm to 70 mm.

The head stem 36 projects approximately 25 mm to 40 mm and exhibits a compound symmetrical tapered surface that includes several flat surfaces 40 and radiused surfaces 42. The surface geometry of the head stem 36 can be varied as desired and may be non-symmetrical, provided the configuration is able to withstand the anticipated loading. The portion of the head stem 36 mounted within a bore 37 of the ball head 38 exhibits a taper, presently a conventional Morris taper. The bore 37 of the ball head 38 is fitted over the tapered head stem 36 to achieve a "suction" fit.

Figure 9:
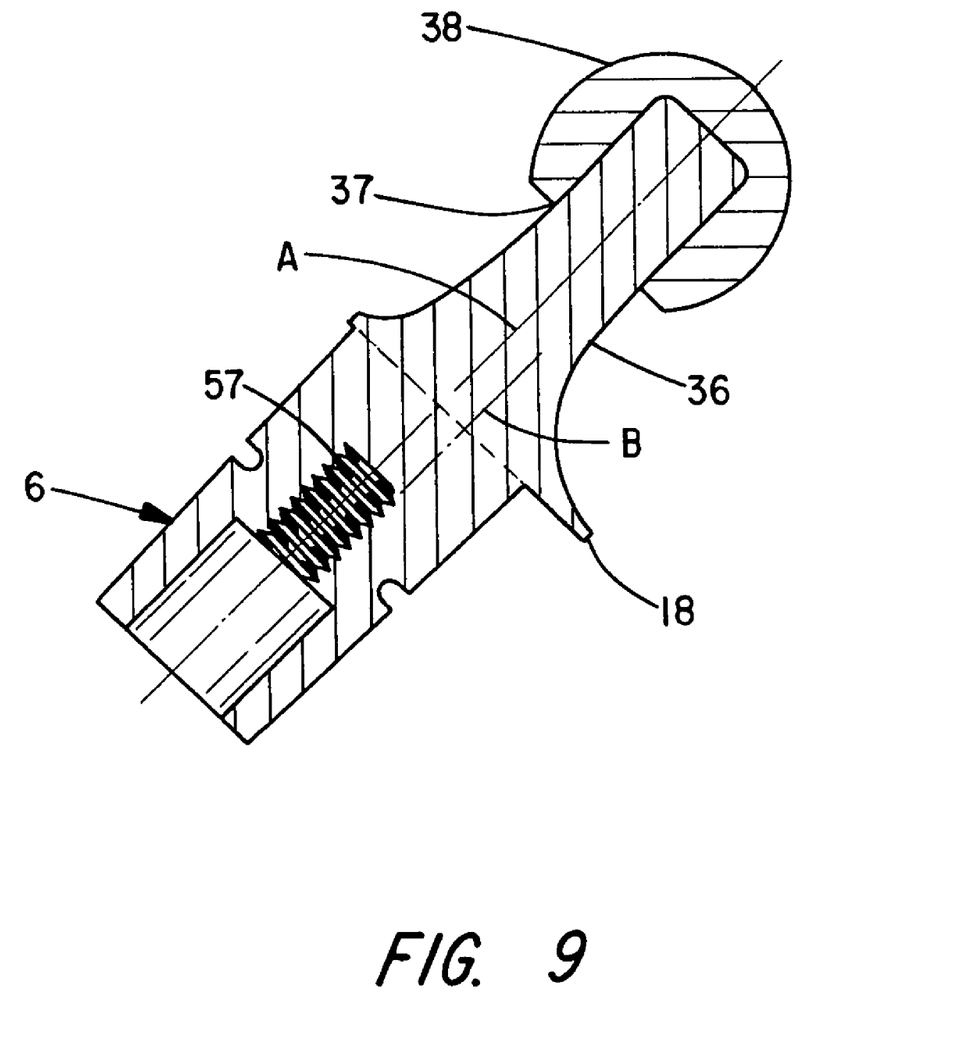
FIG. 9 shows a longitudinal cross section view through a femoral neck subassembly wherein the head stem recesses into a relatively deep bore at an interchangeable ball head.
Figure 10:
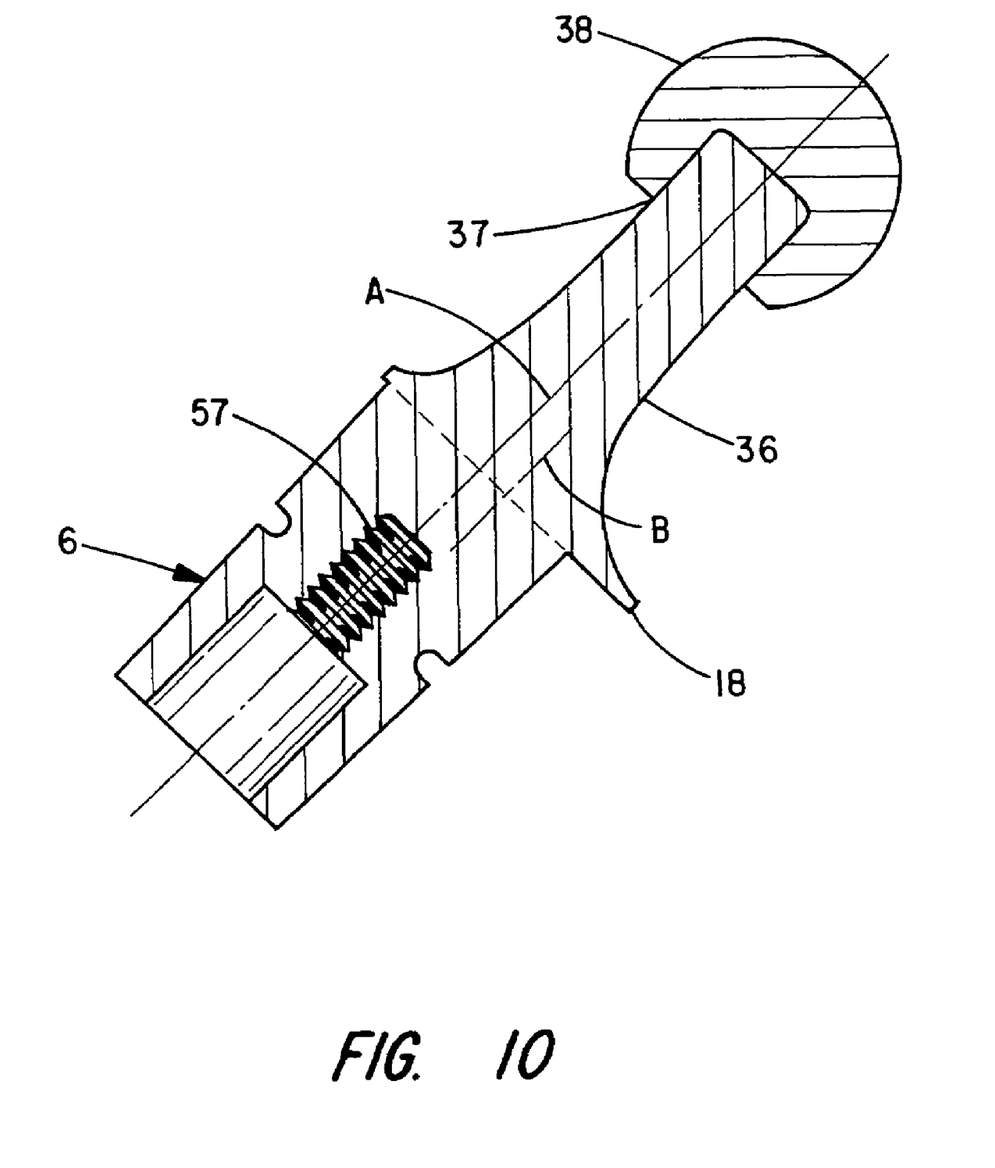
FIG. 10 shows a longitudinal cross section view through a femoral neck subassembly wherein the head stem recesses mid-way into a bore at an interchangeable ball head.
Figure 11:
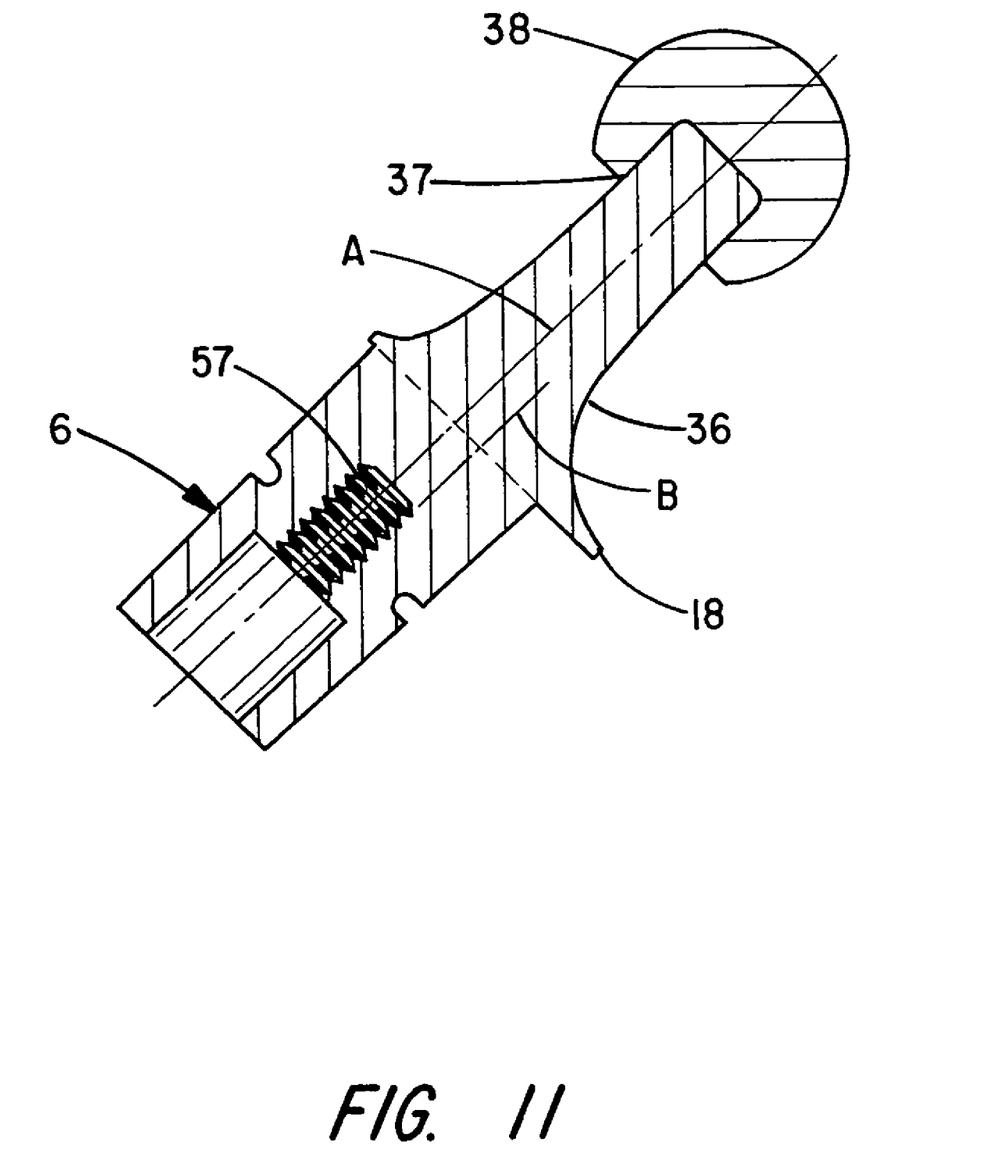
FIG. 11 shows a longitudinal cross section view through a femoral neck subassembly wherein the head stem recesses into a relatively shallow bore at an interchangeable ball head.

FIGS. 9, 10 and 11 depict alternative cross section views to several ball heads 38, each having a bore 37 of differing depth that can interchangeably mate with the head stem 36. The stability of the prosthesis and the length of the femoral neck can thereby be adjusted to accommodate each patient. The use of interchangeable ball heads is deemed preferred to fabricating and inventorying ball head subassemblies 6 of defined lengths.

The head stem 36 projects from the force plate 18 along the longitudinal axis "A" offset from and parallel to a longitudinal axis "B" that orthogonally extends from the center of the force plate 18. Other head stem angular alignments may also be provided.

Figure 12:
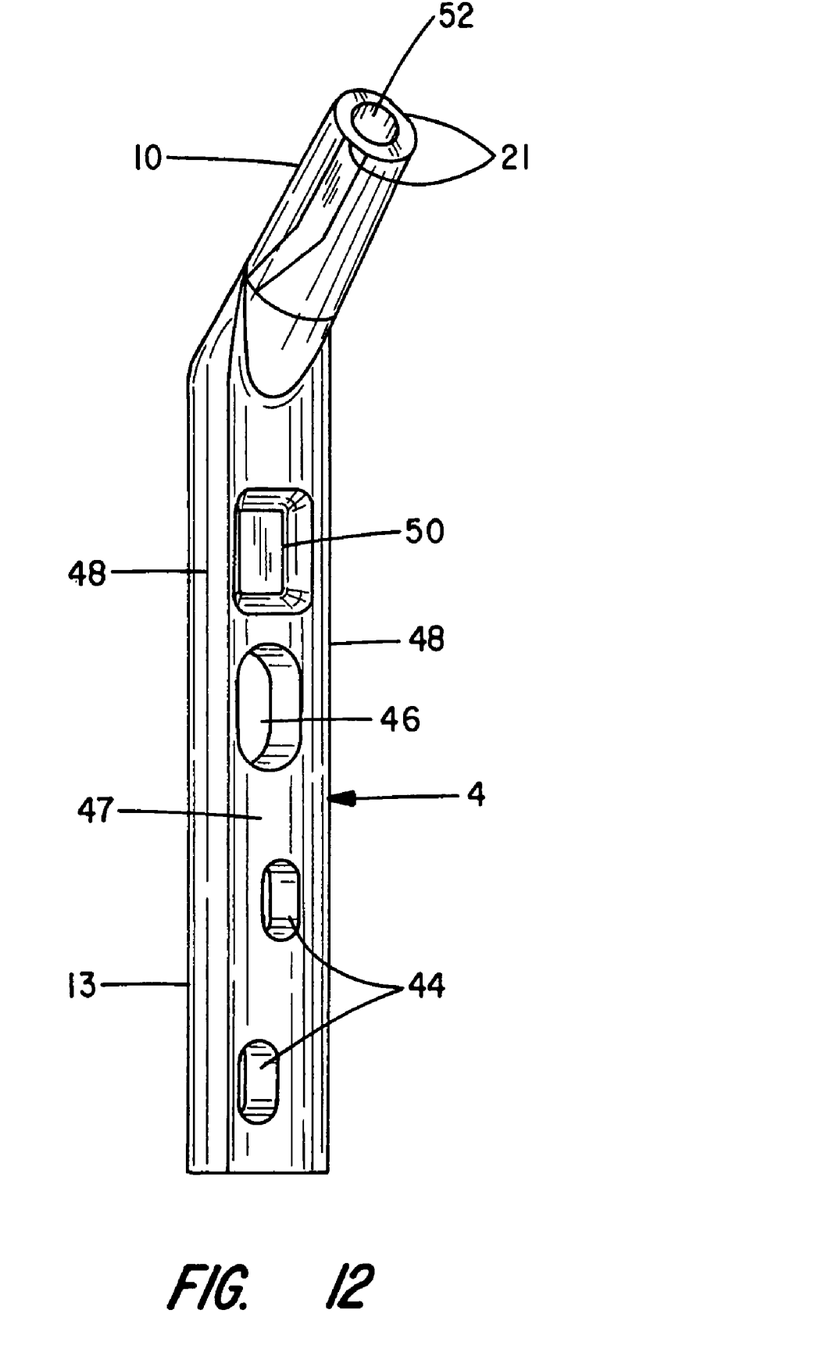
FIG. 12 shows a perspective view of the strap plate rotated to expose the femur-facing or anterior side and a stress relieving recess.

FIGS. 1 and 12 depict views to the outer or dorsal and interior or ventral surfaces of the strap piece 13. The strap piece 13 includes several countersunk, elongated apertures 44 and 46 that are formed to receive appropriate bone screw fasteners 14. The aperture 46 is aligned to the longitudinal centerline of the strap piece 13 and is oversized from the apertures 44.

During normal implant, the first fastener 14 is fitted to the aperture 46 to rough align and secure the strap piece 13 to the femur and the femoral neck or stem piece 10 to the bore 12 in the femoral neck stem base 16 that has been set in the surgically prepared femoral recess. The oversize nature of the aperture 46 facilitates minor lateral and longitudinal adjustments to bring the strap piece 13 into desired contact with the femur. The aperture 46 also acts to decrease proximal strap plate stresses. Other fasteners 14 are successively fitted to the smaller apertures 44 that are laterally displaced to opposite sides of a longitudinal centerline of the strap piece 13 to avoid longitudinal fractures.

The sidewalls 48 of the strap piece 13 and stem piece 10 are radiused to prevent post-operative tissue abrasion or irritation and decrease stress point force build-up. The ventral face of the strap piece 13 includes a longitudinal concavity 47 that mates with the arcuate outer wall of the femur shaft.

Also shown in FIG. 12 at the ventral face of the strap piece 13 adjacent the femur is at least one stress-relieving surface 50. The surface 50 is presently formed as a shaped recess or cavity 50. The recess 50 acts as a stress riser relative to surrounding material and structure. That is, the recess 50 is provided to reduce the stiffness of the strap piece 13 and deflect stress away from the perimeter or sidewalls 48 of the recessed channel and the critical neck region of the stem piece 10.

Figure 13:
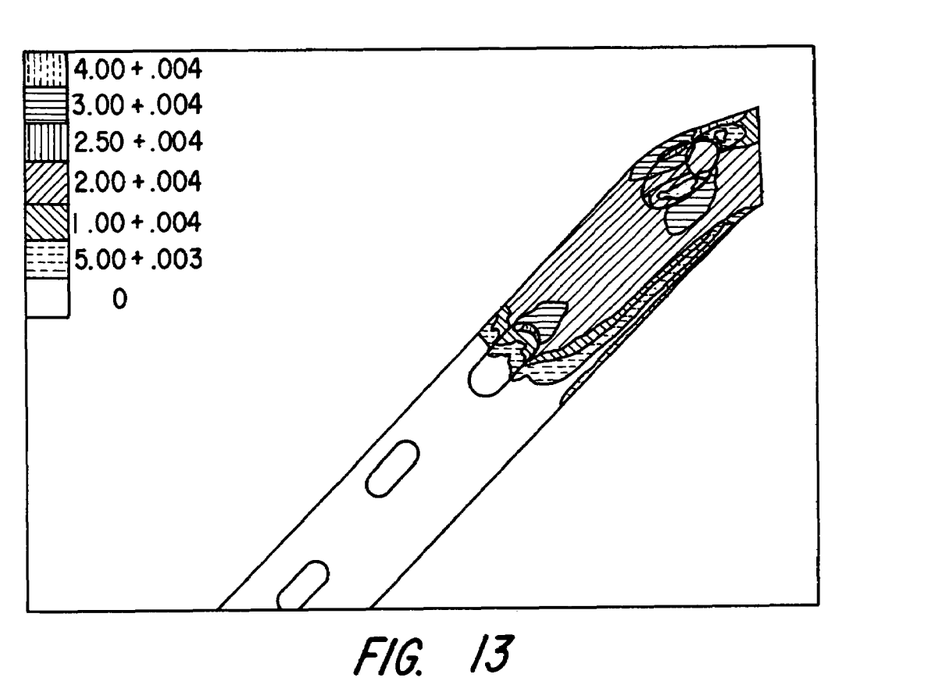
FIG. 13 shows a portion of the outer surface of a strap plate without a stress relieving recess and wherein spectral fringe patterns demonstrate the relatively high stress at the junction of the strap and neckpieces.
Figure 14:
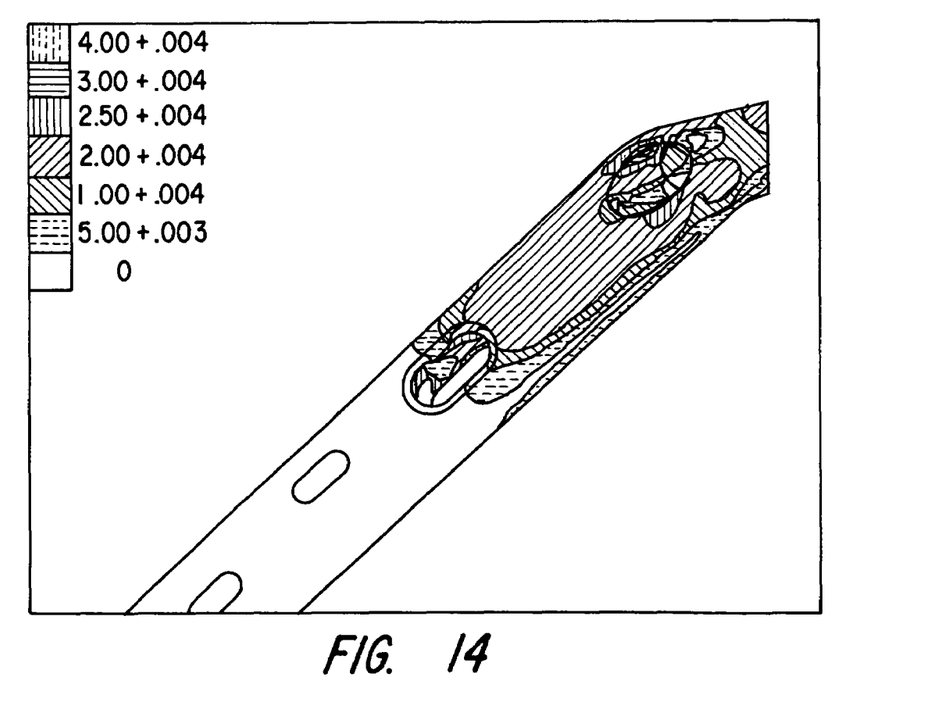
FIG. 14 shows a portion of the outer surface of a strap plate with a stress relieving recess and wherein spectral fringe patterns demonstrate the improved distribution and reduction of stress at the junction of the strap and neckpieces.
Figure 15:
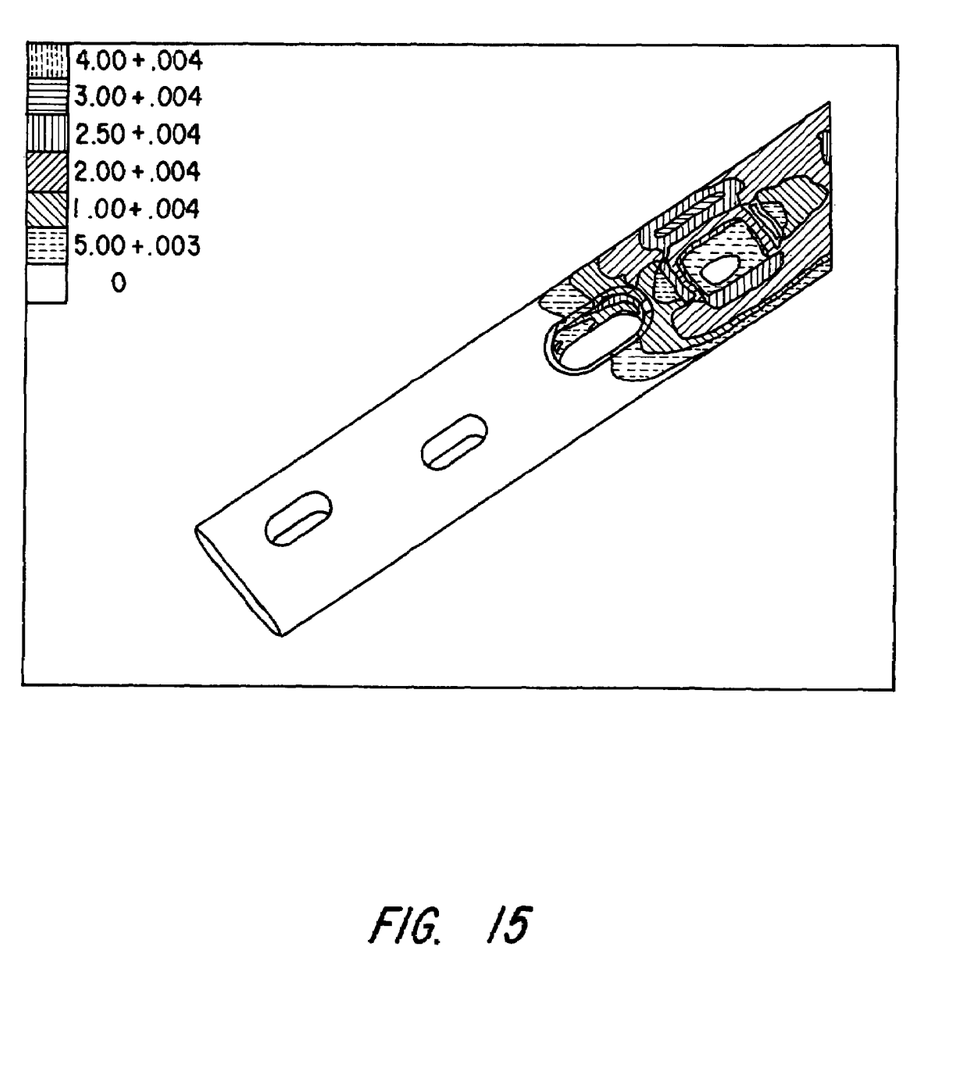
FIG. 15 shows a portion of the interior surface of the strap plate of FIG. 14 with a stress relieving recess and wherein spectral fringe patterns demonstrate the improved distribution and reduction of stress at the junction of the strap and neckpieces.

The reduction and distribution of stress from the neck region is demonstrated from the relative spectral comparison views shown at FIGS. 13, 14 and 15, wherein strap pieces without a recess (FIG. 13) and with a recess 50 (FIGS. 14 and 15) are shown, when placed under stress. The figures particularly demonstrate that stress at the neck was lowered to about 35 ksi and 30 ksi at the first aperture 46 from about 50 ksi at the neck and 40 ksi at the aperture 46. That is, by including a recess 50, stress is shown as being redistributed at FIGS. 14 and 15 away from the neck region and the aperture 46 to the recess 50, where it is less likely to induce a fracture at the juncture of the strap piece 13 to the stem piece 10.

Additional recesses 50, channels and/or other surface treatments may be included at the strap piece 13 to alter the flexibility and stress characteristics of the strap plate 4 to prevent fracture and strengthen the attachment to the ball head subassembly 6. The thickness of the strap piece 13 may also be judiciously varied along its length and/or raised projections can be provided.

Figure 16:
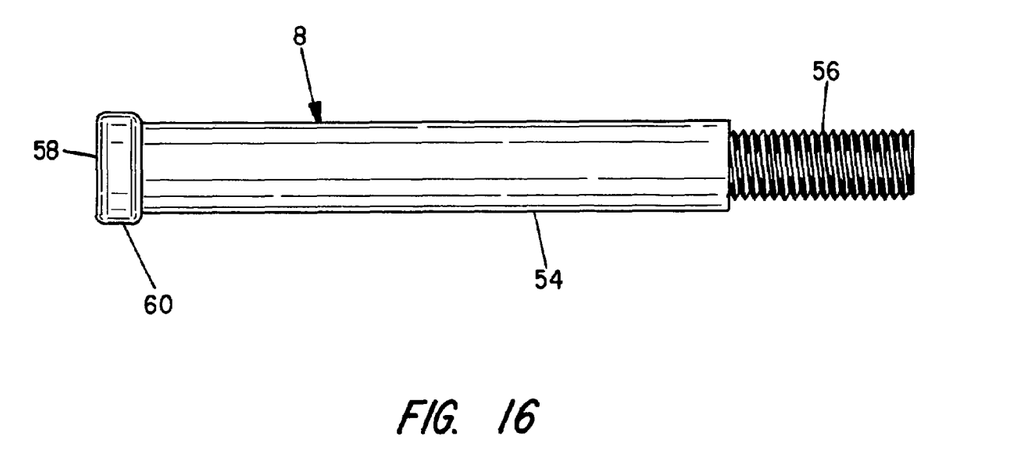
FIG. 16 shows a perspective view of the draw fastener.

FIG. 16 next depicts a view to the draw fastener 8. The fastener 8 mounts through a bore 52 in the femoral neck or stem piece 10 and attaches to the ball head subassembly 6. The opening to the bore 52 is beveled and counter sunk to improve the stress characteristics of the strap plate 4 in the region of the femoral neck 10. The fastener 8 provides a shoulder 54 and a threaded end 56 that mates with internal threads 57 formed into the ball head subassembly 6. The number and pitch of the threads 57 can be varied to assure proper tightening without stripping. A medical grade thread sealant, adhesive or the like and/or other mechanical means (e.g. lock washer) may also be used to prevent loosening over time. A recess 58 is formed into a headpiece 60 to accept a suitable fastener tool (not shown). For example, the recess 58 may exhibit a slot, hexagonal, torqx or Phillips shape and/or the circumferential surface of the head 60 may be shaped to facilitate the draw fastening of the ball head subassembly 6 to the stem piece 10.

While the invention has been described with respect to considered alternative assemblies and considered improvements or alternatives thereto, still other assemblies may be suggested to those skilled in the art. It is also to be appreciated that selected ones of the foregoing components can be used singularly or the various features can be arranged in different combinations to provide a variety of further improved prostheses assemblies. The foregoing description should therefore be construed to include all those embodiments within the spirit and scope of the following claims.

What is claimed is:

1. A hip prosthesis comprising:
  a) a plate member having integral, rigid strap and tubular neck pieces, wherein said strap piece includes a plurality of through bores adapted to receive and support a plurality of screw fasteners at a dorsal surface to secure said strap piece to a femur, wherein said tubular neck piece rigidly projects at an obtuse angle from said strap piece, and wherein said tubular neck piece includes a longitudinal through bore;

b) a stem base having first and second stem pieces that longitudinally project from an intermediate flange piece, wherein said first stem piece is adapted to mount in a recess of the femur, wherein said first stem piece includes a longitudinal bore adapted to receive and support said tubular neck piece, wherein an outer surface of said first stem piece includes a plurality of longitudinally spaced rigid ridges arranges radially about the stem piece, and wherein said flange piece transversely radiates outward from said first and second stem pieces and is adapted to abut the end of the femur;

c) a ball head, wherein said ball head includes a bore adapted to receive an end of said second stem piece and align said ball head to said flange piece; and d) a threaded fastener adapted to mount in the bore of said tubular neck piece and couple to said stem base substantially adjacent said flange piece to draw said flange piece into abutment with said femur.

2. A hip prosthesis as set forth in claim 1 wherein said strap piece includes a concave ventral surface that abuts the femur and wherein said ventral surface includes a recessed cavity located adjacent said neck piece and adapted to relieve stress at the juncture of said strap and tubular neck pieces.

3. A hip prosthesis as set forth in claim 1 wherein said neck piece is shaped to longitudinally align with a portion of the bore of said first stem piece and index said neck and first stem piece in non-rotating engagement with one another.

4. A hip prosthesis as set forth in claim 3 wherein an outer surface of said neck piece is flat and the bore of said first stem piece includes a mating flat surface.

5. A hip prosthesis as set forth in claim 1 wherein said longitudinal ridges are tapered and each ridge includes a V-shaped peripheral edge.

6. A hip prosthesis as set forth in claim 1 wherein each of said longitudinal ridges includes a transecting recess and wherein the recesses of said plurality of ridges are collectively aligned to define a channel.

7. A hip prosthesis as set forth in claim 1 wherein said first and second stem pieces project along a longitudinal axis offset from a longitudinal axis that projects through the center of said flange piece, wherein the end of said second stem piece includes a tapered surface and wherein said ball head includes a bore adapted to mount on the tapered surface.

8. A hip prosthesis as set forth in claim 7 wherein said tapered surface is adapted to mount to a plurality of ball heads having bores of differing depths.

9. A hip prosthesis comprising:

a) a plate member having integral, rigid strap and tubular neck pieces, wherein said strap piece includes a plurality of through bores adapted to receive and support a plurality of screw fasteners at a dorsal surface to secure said strap piece to a femur, wherein said strap piece includes a concave ventral surface that abuts the femur, wherein said ventral surface includes a recessed cavity located adjacent said neck piece and adapted to relieve stress at the juncture of said strap and tubular neck pieces, wherein said tubular neck piece rigidly projects at an obtuse angle from said strap piece, wherein said tubular neck piece includes a longitudinal through bore;

b) a stem base having first and second stem pieces that longitudinally project from an intermediate flange piece, wherein said first stem piece is adapted to mount in a recess of the femur, wherein said first stem piece includes a longitudinal bore adapted to receive and support said tubular neck piece, wherein an outer surface of said first stem piece includes a plurality of longitudinally spaced rigid arranged radially about the stem piece, wherein said flange piece transversely radiates outward from said first and second stem pieces and is adapted to abut the end of the femur;

c) a ball head, wherein said ball head includes a bore adapted to receive an end of said second stem piece and align said ball head to said flange piece; and d) a threaded fastener adapted to mount in the bore of said tubular neck piece and couple to said stem base substantially adjacent said flange piece to draw said flange piece into abutment with said femur.

10. A hip prosthesis as set forth in claim 9 wherein a longitudinal outer surface of said neck piece is shaped to mate with a portion of the longitudinal bore of said first stem piece to prevent rotation of said neck piece within said first stem piece.

11. A hip prosthesis as set forth in claim 9 wherein said longitudinal ridges exhibit a coextensive longitudinal taper.

12. A hip prosthesis as set forth in claim 9 wherein each of said longitudinal ridges includes a recess and wherein the ridge recesses collectively align to define a channel that transects said plurality of longitudinal ridges.

13. A hip prosthesis comprising:

a) a plate member having integral, rigid strap and tubular neck pieces, wherein said strap piece includes a plurality of through bores adapted to receive and support a plurality of screw fasteners at a dorsal surface to secure said strap piece to a femur, wherein said strap piece includes a concave ventral surface that abuts the femur, wherein said ventral surface includes a recessed cavity located adjacent said neck piece and adapted to relieve stress at the juncture of said strap and tubular neck pieces, wherein said tubular neck piece rigidly projects at an obtuse angle from said strap piece, wherein said tubular neck piece includes a longitudinal through bore, and wherein said tubular neck piece includes a flat outer longitudinal surface portion;

b) a stem base having first and second stem pieces that longitudinally project from an intermediate flange piece, wherein said first stem piece is adapted to mount in a recess of the femur, wherein said first stem piece includes a longitudinal bore adapted to receive and support said tubular neck piece, wherein a portion of the longitudinal bore of said first stem piece is flat and mates with the flat surface portion of said neck piece to prevent rotation of said neck piece within said first stem piece, wherein an outer surface of said first stem piece includes a plurality of longitudinal spaced rigid ridges arranged radially about the stem piece, wherein said flange piece transversely radiates outward from said first and second stem pieces and is adapted to abut the end of the femur, and wherein said first and second stem pieces project along a longitudinal axis offset from a longitudinal axis that projects through the center of said flange piece;

c) a ball head, wherein said ball head includes a bore adapted to receive an end of said second stem piece and align said ball head to said flange piece; and d) a threaded fastener adapted to mount in the bore of said tubular neck piece and couple to said stem base substantially adjacent said flange piece to draw said flange piece into abutment with said femur.

14. A hip prosthesis as set forth in claim 13 wherein said first stem piece includes a channel extending transverse to said plurality of longitudinal ridges.

* * * * *

UNITED STATES PATENT AND TRADEMARK OFFICE
CERTIFICATE OF CORRECTION

PATENT NO. : 7,569,075 B2 Page 1 of 1
APPLICATION NO. : 11/212864
DATED : August 4, 2009
INVENTOR(S) : James F. Johnson et al.

It is certified that error appears in the above-identified patent and that said Letters Patent is hereby corrected as shown below:

Column 8, line 3, "rigid arranged" should read -- rigid ridges arranged --.

Signed and Sealed this

Fifteenth Day of September, 2009

David J. Kappos
*Director of the United States Patent and Trademark Office*